United States Patent
Huryn et al.

[11] Patent Number: 6,030,994
[45] Date of Patent: Feb. 29, 2000

[54] SUBSTITUTED PYRROLES COMPOSITIONS

[75] Inventors: Donna Mary Huryn, Allentown; Dennis Dalton Keith, Montclair, both of N.J.

[73] Assignee: Hoffmann-La Roche Inc., Nutley, N.J.

[21] Appl. No.: 09/166,766

[22] Filed: Oct. 5, 1998

Related U.S. Application Data

[62] Division of application No. 08/899,852, Jul. 24, 1997, Pat. No. 5,856,517
[60] Provisional application No. 60/022,079, Jul. 29, 1996, and provisional application No. 60/048,493, Jun. 3, 1997.

[51] Int. Cl.[7] .......................... A61K 31/40; A61K 31/405
[52] U.S. Cl. .......................... 514/414; 514/415; 514/423
[58] Field of Search .................... 548/455, 458, 548/510; 514/414, 415, 423

[56] References Cited

U.S. PATENT DOCUMENTS

| | | | |
|---|---|---|---|
| 5,057,614 | 10/1991 | Davis et al. | 548/466 |
| 5,380,746 | 1/1995 | Barth et al. | 514/414 |

FOREIGN PATENT DOCUMENTS

| | | |
|---|---|---|
| 05039289 | 5/1993 | Japan . |
| WO 9113071 | 9/1991 | WIPO . |
| WO 93/18765 | 9/1993 | WIPO . |
| WO 93/24491 | 12/1993 | WIPO . |

OTHER PUBLICATIONS

Am. J. Hygiene vol. 27, pp. 493–497, 1938.
Bull. Soc. Chim. Belg. 87 (1978) pp. 229–238.
Sulfur Lett. 1983, 1, pp. 167–173.
Journal of Medicinal Chem. vol. 35, No. 1, 1992 pp. 177–184.
Abstract corresponding to WO 9113071.
Drug Des. Discovery 10(3) 1993, pp. 231–248.

*Primary Examiner*—Johann Richter
*Assistant Examiner*—Jane C. Oswecki
*Attorney, Agent, or Firm*—George W. Johnston; Patricia S. Rocha-Tramaloni; Robert A. Silverman

[57] ABSTRACT

Compounds of the formula

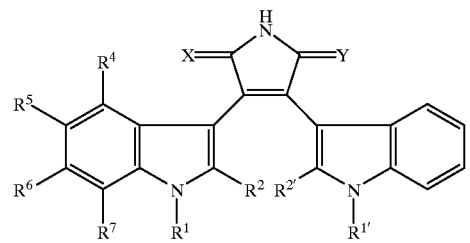

I wherein $R^1$, $R^{1'}$, $R^2$, $R^{2'}$, $R^4$, $R^5$, $R^6$ and $R^7$ are as described herein; as well as pharmaceutically acceptable prodrugs or salts of acidic compounds of formula I with bases and or basic compounds of formula I with acids are antiproliferative agents useful in the treatment of cancer.

10 Claims, No Drawings

SUBSTITUTED PYRROLES COMPOSITIONS

This is a divisional of application Ser. No. 08/899,852, filed Jul. 24, 1997, now U.S. Pat. No. 5,856,517, which claims priority under 35 U.S.C. § 119(e) of provisional applications 60/022,079 and 60/048,493 filed on Jul. 29, 1996 and Jun. 3, 1997, respectively.

BRIEF SUMMARY OF THE INVENTION

The invention relates to substituted pyrroles. More particularly, the invention relates to substituted pyrroles of the formula

I wherein
$R^1$ and $R^{1'}$ are independently alkyl, aryl, alkenyl or alkynyl;
$R^2$ and $R^{2'}$ are independently hydrogen or alkyl;
$R^4$, $R^5$, $R^6$ and $R^7$ each independently are $$CH_2OCR^8,$$
$$\quad\quad O$$

$CO_2R^9$, $CH_2OR^{10}$, CHO, $CH_2NR^{11}R^{12}$, $CON(R^{13})_2$, hydrogen, halogen, cyano, alkyl, hydroxy, alkoxy, aryloxy, haloalkyl, nitro, amino, acylamino, aralkyloxy, monoalkylamino, dialkylamino, alkylthio, alkylsulphinyl or alkylsulphonyl, provided that at least one of $R^4$, $R^5$, $R^6$ or $R^7$ is cyano, $$CH_2OCR^8,$$
$$\quad\quad O$$

$CO_2R^9$, $CH_2OR^{10}$, $CH_2NR^{11}R^{12}$, CHO or $CON(R^{13})^2$;
$R^8$ is alkyl, aralkyl or aryl;
$R^9$ is alkyl, aralkyl or aryl;
$R^{10}$ is hydrogen, alkyl, aralkyl or aryl;
$R^{11}$ and $R^{12}$ are independently hydrogen, alkyl, aryl, aralkyl or acyl;
$R^{13}$ is hydrogen, alkyl, aryl or aralkyl; and
one of X and Y signifies O and the other signifies O, S, (H,OH) or (H,H); as well as pharmaceutically acceptable prodrugs or pharmaceutically acceptable salts of acidic compounds of formula I with bases and or basic compounds of formula I with acids.

The compounds of formula I and their pharmaceutically acceptable salts are anti-proliferative agents useful in the treatment or control of cancer, particularly in the treatment or control of solid tumors. The compounds of the invention are especially useful in the treatment or control of breast tumors and colon tumors.

DETAILED DESCRIPTION OF THE INVENTION

The invention relates to substituted pyrroles. More particularly, the invention relates to substituted pyrroles of the formula

I wherein
$R^1$ and $R^{1'}$ are independently alkyl, aryl, alkenyl or alkynyl;
$R^2$ and $R^{2'}$ are independently hydrogen or alkyl;
$R^4$, $R^5$, $R^6$ and $R^7$ each independently are $$CH_2OCR^8,$$
$$\quad\quad O$$

$CO_2R^9$, $CH_2OR^{10}$, CHO, $CH_2NR^{11}R^{12}$, $CON(R^{13})_2$, hydrogen, halogen, cyano, alkyl, hydroxy, alkoxy, aryloxy, haloalkyl, nitro, amino, acylamino, aralkyloxy, monoalkylamino, dialkylamino, alkylthio, alkylsulphinyl or alkylsulphonyl, provided that at least one of $R^4$, $R^5$, $R^6$ or $R^7$ is $$CH_2OCR^8,$$
$$\quad\quad O$$

$CO_2R^9$, $CH_2OR^{10}$, $CH_2NR^{11}R^{12}$, CHO or $CON(R^{13})_2$;
$R^8$ is alkyl, aralkyl or aryl;
$R^9$ is alkyl, aralkyl or aryl;
$R^{10}$ is hydrogen, alkyl, aralkyl or aryl;
$R^{11}$ and $R^{12}$ are independently hydrogen, alkyl, aryl, aralkyl or acyl;
R—is hydrogen, alkyl, aryl or aralkyl; and
one of X and Y signifies O and the other signifies O, S, (H,OH) or (H,H); as well as pharmaceutically acceptable salts of acidic compounds of formula I with bases and or basic compounds of formula I with acids.

As used herein, the term "alkyl", alone or in combinations, means a straight or branched-chain alkyl group containing a maximum of 10, preferably a maximum of 5, carbon atoms such as methyl, ethyl, propyl, isopropyl, butyl, sec-butyl, t-butyl and pentyl which is unsubstituted or substituted by one or more substituents selected from the group consisting of hydroxy, alkoxy, amino, halogen, thioalkyl, cyano, carboxy or carboxylic acid derivative or alkylsulphinyl. The term "alkoxy" denotes a group wherein the alkyl residue is as defined above, for example, methoxy, ethoxy, propoxy, isopropoxy, butoxy and t-butoxy and the like. A haloalkyl group can carry one or more halogen atoms, with examples of such groups being chloromethyl and trifluoromethyl. The term "acyl", alone or in combination, means a group derived from an unsubstituted or substituted alkanoic acid containing a maximum of 10, preferably a maximum of 5, carbon atoms for example, acetyl, propionyl, butyryl., trifluoroacetyl, chioroacetyl, trichloroacetyl, aminoacetyl or 2-amino-propionyl and the like or from an unsubstituted or substituted aromatic carboxylic acid for example, benzoyl. Examples of substituents on alkanoic acid include one or more of the following: hydroxy, alkoxy, amino, halogen, thioalkyl, cyano, carboxy, carboxylic acid derivative or alkyl sulphinyl and the like. Examples of substituents on aromatic carboxylic acid include one or more of the following: halogen, alkyl, hydroxy, benzyloxy, alkoxy, haloalkyl, nitro, amino, cyano and the like. The term "aryl", alone or in combinations means an unsubstituted phenyl group or a phenyl group carrying one or more, preferably one to three, substituents, examples of which are halogen, alkyl, hydroxy, benzyloxy, alkoxy, haloalkyl, nitro, amino and cyano. The term "halogen" means fluorine, chlorine, bromine or iodine. The term a "carboxylic acid derivative" means an ester, amide, cyano, acid chloride and the like. The term "alkenyl" refers to straight or branched chain hydrocarbon groups of 2 to 5 carbon atoms having at least one double bond. Groups of 3 to 5 carbon atoms are preferred. The term "alkynyl" refers to straight or branched chain hydrocarbon groups of 2 to 5 carbon atoms having at least one triple bond. Groups of 3 to 5 carbon atoms are preferred.

As used herein "pharmaceutically acceptable prodrug" means a compound that may be converted under physiological conditions or by solvolysis to a compound of formula I or to a pharmaceutically acceptable salt thereof.

In formula I above, $R^1$ and $R^{1'}$ are preferably alkyl. In an especially preferred embodiment, $R^1$ and $R^{1'}$ are preferably methyl.

Preferably, one of $R^4$, $R^5$, $R^6$ and $R^7$ is cyano,

$CO_2R^9$, $CH_2OR^{10}$, $CH_2NR^{11}R^{12}$, CHO, or $CON(R^{13})_2$ and the others are hydrogen.

In a particularly preferred embodiment, $R^6$ is cyano,

$CO_2R^9$, $CH_2OR^{10}$, $CH_2NR^{11}R^{12}$, CHO, or $CON(R^{13})_2$ and $R^4$, $R^5$ and R are hydrogen.

Particularly preferred compounds of formula I are those in which $R^1$ is methyl, $R^2$ is hydrogen, $R^{1'}$ methyl, $R^{2'}$ is hydrogen, $R^4$, $R^5$, $R^7$ are hydrogen and $R^6$ is cyano,

$CO_2R^9$, $CH_2OR^{10}$, $CH_2NR^{11}R^{12}$, $CON(R^{13})_2$ or CHO.

In especially preferred compounds, $R^1$ is methyl, $R^2$ is hydrogen, $R^{1'}$ is methyl, $R^{2'}$ is hydrogen, $R^4$, $R^5$, $R^7$ are hydrogen and $R^6$ is cyano,

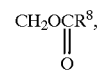

$CO_2R^9$, $CH_2OR^{10}$, $CH_2NR^{11}R^{12}$, $CON(R^{13})_2$ and CHO wherein $R^8$ and $R^9$ are alkyl, preferably methyl, $R^{10}$ is alkyl, preferably methyl or hydrogen and $R^{11}$, $R^{12}$ and $R^{13}$ are hydrogen.

The compounds of formula I in which X and Y both signify O, are prepared by the following Scheme I

SCHEME I

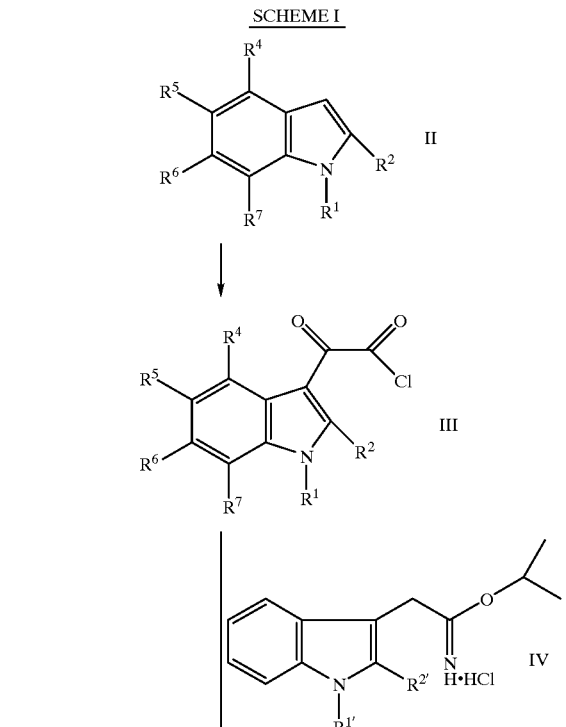

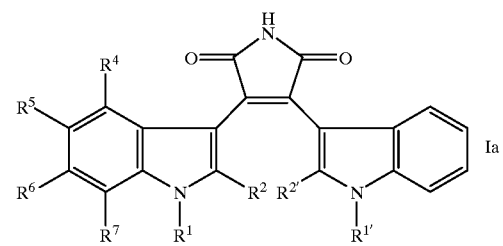

wherein $R^1$, $R^{1'}$, $R^2$, $R^{2'}$, $R^4$, $R^5$, $R^6$ and $R^7$ are as described above; provided that when any of $R^1$, $R^{1'}$, $R^2$, $R^{2'}$, $R^4$, $R^5$, $R^6$ or $R^7$ are substituents which react with acid chlorides, such as, for example, when any of $R^1$, $R^{1'}$, $R^2$, $R^{2'}$, $R^4$, $R^5$, $R^6$ or $R^7$ are hydroxy, hydroxyalky, amino, monoalkylarnino or aminoalkyl, such substituent is protected with a conventional protecting group.

As set forth in Scheme I, a compound of formula II, a known compound or compound prepared by known methods, is reacted by conventional methods with oxalyl chloride, conveniently is an inert organic solvent, such as a halogenated aliphatic hydrocarbon, at a temperature of from about 0° C. to the reflux temperature of the solvent to form a corresponding compound of formula III.

The compound of formula III is reacted with a compound of formula IV, a known compound or compound prepared by known methods, and triethylamine in a solvent such as dichloromethane at a temperature of from about 0° to 25° C., then treated with paratoluene sulphonic acid in a solvent such as toluene at a temperature of about 25° C., to give a corresponding compound of formula Ia. If a protecting group was utilized during reaction of a compound of formula III with a compound of formula IV, it is removed at this point using known methods.

A compound of formula I in which one of X and Y signifies O and the other signifies (H,OH), is prepared by reducing a compound of formula I in which X and Y both signify O (formula Ia) with a complex metal hydride.

The reduction can be carried out in a known manner including the protection of substituents on the indole ring prior to reduction and deprotection after reduction according to known methods. An alkali metal aluminum hydride such as lithium aluminum hydride is preferably used as the complex metal hydride, although other hydrides such as diisobutylaluminum hydride and sodium dihydro-bis(2-methoxy-ethoxy)aluminate can also be used. Suitable inert organic solvents in which this reduction can be carried out include aliphatic and cyclic ethers such as diethyl ether or tetrahydrofuran (THF) and hydrocarbons such as hexane, benzene and toluene. Conveniently, this reduction is carried out at about room temperature.

A compound of formula I in which one of X and Y signifies O and the other signifies (H,H), can be prepared by catalytically hydrogenating a compound of formula I in which one of X and Y signifies O and the other signifies (H,OH).

Conventional procedures can be used in carrying out the catalytic hydrogenation including the protection and deprotection of substituents on the indole ring according to known procedures.

Thus, the catalytic hydrogenation can be carried out in the presence of a noble metal catalyst such as a palladium or platinum catalyst, for example, palladium/carbon (Pd/C), and an inert organic solvent such as an alkanol (for example, methanol or ethanol). This catalytic hydrogenation is expediently carried out at about room temperature and under atmospheric pressure.

A compound of formula I in which one of X and Y signifies O and the other signifies S, is prepared by reacting a compound of formula I in which X and Y both signify O with a sulfurizing agent.

Conventional procedures can be used in carrying out the sulfurization including the protection of substituents prior to the sulfurization and deprotection after the sulfurization, which would be known to those skilled in the art. The sulfurization is conveniently carried out using phosphorous pentasulfide, Lawesson's reagent [2,4-bis(4-methoxyphenyl)-1,2-dithioxo-1,3,2,4-dithia-phosphetane: Bull. Soc. Chim. Belg. 87 (1978) 229–238] or Davy Reagent [2,4-bis(methylthio)-1,3,2,4-dithiadiphosphetane; Sulfur. Lett. 1983, 1, 167]. This reaction is conveniently carried out in an inert organic solvent such as an aliphatic or cyclic ether (for example, dimethoxyethane) or an aromatic hydrocarbon which may be halogenated (for example, benzene, toluene or chlorobenzene) and at an elevated temperature, especially at the reflux temperature of the reaction mixture.

If desired, an acidic compound of formula I can be converted into a pharmaceutically acceptable salt with a base or a basic compound of formula I can be converted into a pharmaceutically acceptable salt with an acid.

The conversion of an acidic compound of formula I into a pharmaceutically acceptable salt can be carried out by treatment with a suitable base in a known manner. Suitable salts are those derived not only from inorganic bases, for example, sodium, potassium or calcium salts, but also from organic bases such as ethylenediamine, monoethanolamine or diethanolamine. The conversion of a basic compound of formula I into a pharmaceutically acceptable salt can be carried out by treatment with a suitable acid in a known manner. Suitable salts are those derived not only from inorganic acids, for example, hydrochlorides, hydrobromides, phosphates or sulphates, but also from organic acids, for example, acetates, citrates, fumarates, tartrates, maleates, methanesulphonates or p-toluenesulphonates.

The pyrroles of formula I and their pharmaceutically acceptable salts inhibit cellular processes, for example cell proliferation, and can be used in the treatment or control of inflammatory disorders such as arthritis, immune diseases, in conjunction with organ transplants and in oncology.

The epithelial breast carcinoma cell line, MDAMB-435, and the colon carcinoma cell line, SW480, were purchased from ATCC (American Type Cell Culture Collection) and were grown in culture in medium as recommended by ATCC. For analysis of the effect of various compounds on growth of these cells, the cells were plated at a concentration of 1500 cells/well in a 96 well tissue culture plate ("test plate"). The day after the cells were plated, the compounds to be analyzed were dissolved in 100% DMSO (dimethyl sulfoxide) to yield at 10 mM stock solution. Each compound was diluted in $H_2O$ to 1 mM and was added to triplicate wells in the first row of a 96 well master plate which contains medium to yield a final concentration of 40$\mu$M. The compounds were then serially diluted in medium in the "master plate". The diluted compound(s) were then transferred to test plates containing cells. A row of vehicle "control cells" received DMSO. The final concentration of DMSO in each well was 0.1%. At day 5 post-drug addition, the plates containing MDA-MB435 cells were analyzed as follows. Plates containing SW480 cells were analyzed at day 7 post drug addition as follows.

MTT (3-(4-5 methyl thiazole-2-yl)-2,5-diphenyl tetrazolium bromide; thiazolyl blue) was added to each well to yield a final concentration of 1 mg/ml. The plate was then incubated at 37° C. for 2½–3 hours. The MTT containing medium was then removed and 50$\mu$l of 100% ethanol was added to each well to dissolve the formazan. The absorbences were then read using an automated plate reader (Bio-tek microplate reader). $IC_{50}$'s were calculated using the Reed and Munsch equation, see Am. J. Hygiene Vol. 27 pgs. 493–497, 1938.

The results are provided in the Table below.

TABLE

| | Antiproliferative Activity Cell Line | |
|---|---|---|
| Compound | MDAMB435 $IC_{50}$ $\mu$M | SW480 $IC_{50}$ $\mu$M |
| Ex 3 | 0.3 | 0.83* |
| Ex 4a | 0.01* | 0.01* |
| Ex 4b | 0.032 | 0.054 |
| Ex 1 | 0.03 | 0.008 |
| Ex 4c | 0.07* | 0.11* |
| Ex 5 | 0.42 | 0.35* |
| Ex 6 | 0.7* | not tested |

*An average of two separate experiments.

The pyrroles of formula I and their aforementioned salts can be used as medicaments, for example, in the form of pharmaceutical preparations, which can be administered orally, for example, in the form of tablets, coated tablets, dragees, hard or soft gelatin capsules, solutions, emulsions or suspensions. They can also be administered rectally, for example, in the form of suppositories or parenterally, for example, in the form of injection solutions.

For the manufacture of pharmaceutical preparations these compounds can be formulated with therapeutically inert, inorganic or organic carriers. Lactose, maize starch or derivatives thereof, talc, steric acid or its salts can be used as such carriers for tablets, coated tablets, dragees and hard gelatin capsules. Suitable carriers for soft gelatin capsules are vegetable oils, waxes, fats, semi-solid or liquid polyols. Depending on the nature of the active substance no carriers are, however, generally required in the case of soft gelatin capsules. Suitable carriers for the manufacture of solutions and syrups are, water, polyols, saccharose, invert sugar and glucose. Suitable carriers for injection solutions are water, alcohols, polyols, glycerine and vegetable oils. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

As mentioned above, the pyrroles of formula I and their aforementioned salts can be used in the treatment or control of oncological, inflammatory, immunological, bronchopulmonary and cardiovascular disorders. The dosage can vary within wide limits and will, or course, be adjusted to the individual requirements in each particular case. In general, in the case of oral or parenteral administration to adult humans, a daily dosage of about 5 mg to 5000 mg should be appropriate, although the upper limit may be exceeded when this is found to be expedient. The daily dosage can be administered as a single dose or in divided doses, or for parenteral administration, it may be given as continuous infusion.

The following Examples illustrate the present invention:

EXAMPLE 1

1-methyl-3-[4-(1-methyl-1H-indol-3-yl)-2,5-dioxo-2,5-dihydro-1H-pyrrol-3-yl]-1H-indole-6-carbonitrile 1-methyl-1H-indole-6-carbonitrile (1.0 g, 6.4 mmole), a known compound, was dissolved in ethyl ether ($Et_2O$) (25 mL), chilled in an ice bath and treated with oxalyl chloride (0.95 mL, 10.9 mmole, 1.7 equiv.). After removal of the ice bath, yellow solids soon precipitated. This mixture was stirred at room temperature overnight, the solids were then collected and washed with ethyl ether and dried under vacuum for 30 minutes to provide 1.53 g (96%) of(6-cyano-1-methyl-1H-indol-3-yl)oxo-acetyl chloride. This material (1.53 g, 6.2 mmole) along with 2-(1-methyl-1H-indol-3yl)-acetimidic acid isopropyl ester hydrochloride (1.66 g, 6.2 inmole, 1 equiv.) was suspended in $CH_2Cl^2$ (100 mL) and cooled in an ice bath. The mixture was treated with $Et_3N$ (3.5 mL, 24.8 mmole, 4 equiv.), stirred at 0° for 30 minutes. then at room temperature for an additional 3 hours. The reaction mixture was then diluted with $CH_2Cl^2$ (150 mL), washed with $H_2O$(50 mL), and then 0.5N HCl (50 mL). The organic fractions were dried over $MgSO_4$, filtered and evaporated to give a dark oil. The residue was taken up in toluene (30 mL), chilled in an ice bath, then treated with pTsOH(1.3 g, 6.8 mole, 1.1 equiv.), then stirred at room temperature for 2 hours. The red solids which precipitated were collected, washed with a small volume of toluene, hexane, the $H_2O$, then partitioned between 500 mL $CH_2Cl_2$ and 75 mL saturated $NaHCO_3$. The organic layer was dried over $MgSO_4$, filtered and evaporated to provide 2 g of a red solid. The solid was washed with cold $CH_2Cl_2$, then recrystallized from acetone/hexane to give 938 mg of 1-methyl-3-[4-(1-methyl-1H-indol-3-yl)-2,5-dioxo-2,5-dihyclro-1H-pyrrol-3-yl]-1H-indole-6-carbonitrile.

EXAMPLE 2

1-methyl-3-[4-(1-methyl-1H-indol-3-yl)-2,5-dioxo-2,5-dihydro-1H-pyrrol-3yl]-1H-indole-5-carbonitrile 1-methyl-1H-indole-5-carbonitrile, a known compound, (0.4 g, 2.55 mmole) was dissolved in ethyl ether (25 mL), chilled in an ice bath and treated with oxalyl chloride (0.35 mL, 4.0 mmole, 1.6 equiv.). This mixture was stirred at room temperature overnight, then the solvent was removed by evaporation, and evaporated from $CH_2Cl_2$ again. This residue along with 2-(1-methyl-1H-indol-3yl)-acetimidic acid isopropyl ester hydrochloride (0.68 g, 2.55 mmole, 1 equiv.) was suspended in $CH_2Cl^2$ (50 mL) and cooled in an ice bath. The mixture was treated with triethylamine $Et_3N$ (1.4 mL, 10 mmole, 4 equiv.) stirred at 0° for 30 minutes, then at room temperature for an additional 3 hours. The reaction mixture was then diluted with $CH_2Cl^2$ (100 imL), washed with $H_2O$ (25 mL), and then 0.5N HCl (25 mL). The organic fractions were dried over $MgSO_4$, filtered and evaporated to give a dark oil. The residue was taken up in toluene (50 mL), chilled in an ice bath, then treated with pTsOH (0.53 g, 2.8 mmole, 1.1 equiv.), then stirred at room temperature overnight. The toluene was evaporated, and the residue dissolved in $CH_2Cl_2$ (100 mL), then washed with saturated $NaHCO_3$ (30 mL), $H_2O$ (30 mL), and brine (30 mL). The organic layer was dried over $MgSO_4$, filtered and evaporated, then purified by flash column chromatography (10% ethyl acetate (EtOAc)/Hexane). The product was firther purified by washing with cold $CH_2Cl_2$ to provide 0.43 g of 1-methyl-3-[4-(1-methyl-1H-indol-3-yl)-2,5-dioxo-2,5-dihydro-1H-pyrrol-3yl]-1-H-indole-5-carbonitfile.

EXAMPLE 3

Acetic acid 1-methyl-3-[4-(1-methyl-1H-indol-3-yl)-2,5-dioxo-2,5-dihydro-1H-pyrrol-3-yl]-1H-indole-6-yl methyl ester a) Acetic acid 1-metihyl-1H-indol-6-yl methyl ester
NaH(8.2 mm) in N,N-dimethylformamide ("DMF") (20 mL) was cooled to 0° C., then treated with a solution of the known 1H-indole-6-methanol (1 g,6.8 mm) in DMF(8 mL). After stirring for 1 hour at 0° C., methyl iodide ("MeI") (0.51 mL, 8.2 mm) dissolved in DMF (2 mL) was added, and the mixture was stirred at 0° C. overnight, then poured into ice/$H_2O$(250 ml) and extracted with EtOAc(50 mL×3). The organic fraction was dried over $MgSO_4$, filtered, evaporated and purified by flash column chromatography to afford 1-methyl-1H-indole-6-methanol (0.82 g. 75%). This product (1-methyl-1H-indole-6-methanol, 1 g, 6.2 mm) was dissolved in a mixture of pyridine (5 mL) and acetic anhydride ($Ac_2O$) (5 mL) and stirred at room temperature overnight. The solvent was evaporated, and the residue purified by flash column chromatography to afford 1.09 g of Acetic acid 1-methyl-1H-indol-6-yl methyl ester.

b) Acetic acid 1-methyl- 1H-indol-6-yl methyl ester (1.09 g, 5.7 mm) was dissolved in $Et_2O$ (30 mL), cooled to 0° C., and treated with oxalyl chloride (0.87 mL, 10 mm). The niixture was allowed to stir overnight while warming to room temperature. The yellow precipitate was collected, washed with Et₂O and dried to give 1. 5 g of the glyoxalyl chloride adduct, Acetic acid 3-chlorocarbonecarbonyl-1-methyl-1H-indol-6-yl methyl ester. The glyoxalyl chloride adduct (1.5 g, 5 mm) and 2-(1-methyl-1H-indol-3-yl) ethanimidic acid isopropyl ester hydrochloride (1.3 g, 5 mm) were combined with CH₂Cl₂ (30 mL), cooled to 0° C., and treated with Et₃N (2.84 mL,20 mm). After allowing to warm to room temperature overnight, the reaction mixture was diluted with CH₂Cl₂, extracted with H₂O(50 mL), and 0.5M Hcl (50 mL). The organic layer was dried over MgSO₄, filtered and evaporated to yield a red solid. This material was combined with toluene (70mL) and treated with para-toluene sulphonic acid (pTsOH) (1 g, 5.5 mm), then stirred for three hours. After filtration, the insoluble material was washed with toluene then dissolved in CH₂Cl₂ (250 mL) and extracted wtih NaHCO₃ (2×200 mL). The organic layer was dried over MgSO₄, filtered and evaporated to afford a red residue. This residue was furoom temperatureher purified by washing with EtOAc and cold acetone to provide Acetic acid 1-methyl-3-[4-(1-methyl-1H-indol-3-yl)-2,5-dioxo-2,5-dihydro-1H-pyrrol-3-yl]-1H-indol-6-yl methyl ester; mp=271° C.

EXAMPLE 4

The following were prepared in a manner similar to that in Example 3b.
a) 1-methyl-3-[4-(1-methyl-1H-indol-3-yl)-2,5-dioxo-2,5-dihydro-1H-pyrrol-3-yl]-1H-indole-6-carboxylic acid methyl ester; mp=245° C. from 1-methyl-1H-indole-6-carboxylic acid methyl ester.
b) 1-methyl-3-[4-(1-methyl-1H-indol-3-yl)-2,5-dioxo-2,5-dihydro-1H-pyrrol-3-yl]-1H-indole-6-carboxaldehyde; mp=241° C. from 1-methyl-1H-indole-6-carboxaldehyde.
c) 3-(6-Methoxymethyl-1-methyl-1H-indol-3-yl)-4-(1-methyl-1H-indol-3-yl)-pyrrole-2,5-dione; mp=216–17° C. from 6-methoxymethyl-1-methyl-1H-indole.

6-methoxy:methyl- 1-methyl-1H-indole was prepared according to the following procedure:

A solution of the known 1H-indole-6-methanol (0.5 g, 3.4 mm) in DMF (30 mL) was treated with NaH (8.16 mm) at 0° C. After stirring for 1 hour, the mixture was treated wtih a solution of MeI (0. 5nL, 8.1 mm) in DMF(2 mL). The mixture was allowed to warm to room temperature overnight, then poured in H₂O (150mL), and extracted with CH₂Cl₂ (50 mL×3). The organic layer was dried over MgSO₄, filtered and evaporated. Purification via flash column chromatography afforded 0.28 g of 6-methoxymethyl-1-methyl-1H-indole.

EXAMPLE 5

3-(6-hydroxymethyl-1-methyl-1H-indol-3-yl)-4-(1-methyl-1H-indol-3-yl)pyrrole-2,5-dione Acetic acid 1-methyl-3-[4-(1-methyl-1H-indol-3-yl)-2,5-dioxo-2,5-dihydro-1H-pyrrol-3-yl]-1H-indol-6-yl methyl ester (0.87 g, 2 mm) was combined with a solution of Et₃N/H₂O/methanol (MeOH) (5:4:1) and heated at ~50° C. until tlc indicated the disappearance of starting material. After evaporation of the solvent, the residue was dissolved in CH₂Cl₂ (150 mL) and extracted with H₂O (50 mL), 0.05 M HCl (50 mL) and saturated NaHCO₃ solution (50 mL). The organic layer was dried over MgSO₄, filtered and evaporated. Crystallization from EtOAc provided 0.35 g of 3-(6-hydroxymethyl-1-methyl-1H-indol-3-yl)-4-(1-methyl-1H-indol-3-yl)pyrrole-2,5-dione; mp=245–246° C.

EXAMPLE 6

1-Methyl-3-[4-(1-methyl-1H-indol-3-yl)-2,5-dioxo-2,5-dihydro-1H-pyrrol-3-yl]-1H-indole-6-carboxylic acid amide A mixture of 0.7 g (1.84 mmol) of 1-methyl-3-[4-(1-methyl-1H-indol-3yl)-2,5-dioxo-2,5-dihydro-1H-pyrrol-3-yl]-1H-indole-6-carbonitrile, 2.4 g (15.6 mmol) of sodium perborate tetrahydrate in 15 ml of water, and 250 ml of methanol was heated at 50° C. under argon for 2 days. After removal of most of the solvent under vacuum, the residue was diluted with water and extracted with ethyl acetate. The organic phase was washed with brine, dried over MgSO₄ and concentrated to give 0.6 g of a red solid material which was refluxed in ethyl acetate. The suspension was placed in a freezer and the red solid collected by filtration, giving 154.3 mg (21%) of pure 1-methyl-3-[4-(1-methyl-1H-indol-3-yl)-2,5-dioxo-2,5-dihydro-1 H-pyrrol-3-yl]-1H-indole-6-carboxylic acid amide; mp=176–182° C. (d).

EXAMPLE 7

1-Methyl-3-[4-(-methyl-1H-indol-3-yl)-2 ,5-dioxo-2, 5-dihydro-1H-pyrrrol-3-yl]-1H-indole-6-carboxylic acid ethyl ester a) 1-Methyl-6-cyanoindole (3.12 g, 21.9 mmole) was heated at reflux in 180 mL of ethanol/water (8:1) containing 15 g of potassium hydroxide to give 3.0 g of 1-methyl-1H-indole-6-carboxylic acid as a white solid.
b) A solution of 1.05 g (6.0 mmol) of 1-methyl-1H-indole-6-carboxylic acid in 15 mL of methylene chloride was added to a stirring solution of 1.905 g (10 mmole) of 1-ethyl-3-(3dimethyl-aminopropyl)carbodiimide hydrochloride, 1.20 g (10 mmole) of 4-dirmethylaminopyridine in 20 mL of methylene chloride at room temperature. Ethanol was added and the reaction stirred for 15 h. The reaction mixture was extracted with ethyl acetate, the organic phase was washed with brine and dried on anhydrous magnesium sulfate. Chrorriatographic purification of this material gave 1.08 g (89%) of 1-methyl-1H-indole-6-carboxylic acid ethyl ester as a pale yellow oil.
c) 1-Methyl-3-[4-(-methyl-1H-indol-3-yl)-2,5-dioxo-2,5-dihydro-1H-pyrrrol-3-yl]-1H-indole-6-carboxylic acid ethyl ester; mp=215–216° C. was prepared from 1-methyl-1H-indole-6-carboxylic acid ethyl ester using a procedure similar to that described in Example 3b.

EXAMPLE 8

3-[1-(2-Propyl)-6-methoxymethyl-1H-indol-3-yl]-4-(1-methyl-1H-indo-3-yl)-pyrrole-2,5-dione a) 10 g (55.2 mmole) of 4-methyl-3-nitro-benzoic acid, 16.8 mL (126.96 mmole) of N,N-dimethylformamide dimethylacetal in anhydrous N,N-dimethyl formamide (50 mL) was heated at 140° C. under argon for 17 h. The reaction mixture was cooled to room temperature and evaporated to a dark red residue, it was dissolved into 70 mL of hot methanol, kept at 25° C. for 3 h and at 4° C. overnight. The crystalline product was filtered and the crystals washed with ice-cold methanol followed by hexanes. They were dried under high vacuum to give 10.6 g (76.9%) of eneamine.
b) A solution of eneamine (10.4 g, 41.5 mmole) in 160 mL of methanol was stirred inder argon and 12.9 mL (101.92 mmole) chlorotrimethylsilane was added dropwise. The resulting light red solution was refluxed for 18 h and tlc in hexanes (65)/ethyl acetate (35) indicated the reaction to be complete. The reaction mixture was evaporated to an oily residue, redissolved into 100 mL of ethyl acetate, extracted with saturated sodium bicarbonate and saturated sodium chloride solutions, dried organic layer over magnesium sulfate and evaporated to an oil. Crystallization from 30 mL of anhydrous ether gave 10.8 g of 4-carbomethoxy-2-nitrophenyl-acetaldehyde dimethylacetal.

c) 4-Carbomethoxy-2-nitrophenylacetaldehyde dimethylacetal (8.75 g, 41.43 mmole) was reduced under hydrogen (50 psi, 0.45 g of 10% Pd/carbon) in 170 mL of methanol for 2.5 h. The solution was filtered through celite and evaporated to an oil. Crystallization from ether and hexanes gave 6.16 g of 2-amino4-carbomethoxy-phenylacetaldehyde dimethylacetal.

d) A solution of 5.9 g (24.66 mmole) of 2-amino4-carbomethoxy-phenylacetaldehyde dimethylacetal in 160 mL of acetic acid was stirred with 4.8 mL (65.12 mmole) of acetone, and anhydrous sodium sulfate (46.24 g, 325.6 minole) for 10 minutes under argon. Sodium triacetoxyborohydride (20.7 g, 97.68 mmole) was added over a period of 2 min and the reaction stirred at 25° C. for 20 min. The reaction mixture was poured slowly into 490 mL of saturated sodium bicarbonate solution, extracted with ethyl acetate. The organic layer was dried over magnesium sulfate. Concekitration of the filtered solution gave an oily residue (6 g) which was purified by flash chromatography (75% ethyl acetate/hexanes) to give 3.8 g of 4-carbomethoxy-2-N-2-propylamino)phenylacetaldehyde dimethylacetal.

e) 4-Carbomethoxy-2-(N-2-propylamino) phenylacetaldehyde dimethylacetal (3.7 g, 13.15 mmole) was refluxed with 100 mL of 1N hydrochloric acid in methanol for 1 h. The solution was concentrated and the residue dissolved in 50 mL of ethyl acetate, washed with saturated sodium bicarbonate solution, dried organic layer over magnesium sulfate and evaporated to give 2.78 g of 6-carbomethoxy-1-(2-propyl)indole.

f) A solution of 0.250 g (1.15 mmole) of 6-carbomethoxy-1-(2-propyl)indole in 2 mL of anhydrous tetrahydrofuran was added dropwise to a stirring slurry of lithium aluminum hydride (52.4 ing 1.38 mmole) in 7 mL of anhydrous tetrahydrofuran under argon it 0° C. and then stirred at 25° C. for 45 min. The solution was cooled to 0° C. and 0.340 mL of methanol was added dropwise, followed by 0.58 mL of 1N sodium hydroxide solution. The slurry was stirred at 25° C. for 15 min. The white precipitate was filtered through celite, and the solution concentrated. The residue was suspended in 20 mL of ethyl acetate and 20 mL of water. The layers were separated. The aqueous layer was back-extracted with ethyl acetate and both ethyl acetate layers were combined and dried over magnesium sulfate. Concentration gave 6-hydroxymethyl-1-(2-prol:)yl)indole as an oil (214 mg).

g) A solution of 6-hydroxymethyl-1-(2-propyl)indole (0.214 g, 1.13 mmole) in 2 mL of anhydrous N,N-dimethylformamide was added dropwise to a slurry of 95% NaH (35.2 mg, 1.36 mmole) in 6 mL of anhydrous N,N-dimethylformamide at 0° C. under argon and the reaction mixture was stirred at 0° C. for 1 h followed by addition of methyl iodide (84.7 mL, 1.356 mmole). The reaction was then stirred at 20° C. under argon for 17 h. It was poured into ice-water (50 mL) and extracted with ethyl acetate. The ethyl acetate layers were dried over anhydrous magnesium sulfate and evaporated. Purification by flash chromatography using ethyl acetate (2–5%)/hexanes gave 107 mg of 6-methoxymethyl-1-(2-p-ropyl) indole.

h) 6-Methoxymethyl-1-(2-propyi)indole was reacted with oxalyl chloride and then 2-(1-methyl-1H-indol-3-yl) ethanimidic acid isopropyl ester hydrochloride as described in Example 3b to yield 3-[1-(2-propyl)-6-methoxymethyl-lH-indol-3-yl]-4-(1-methyl-1H-yl)-pyrrole-2,5-dione.

EXAMPLE 9

TABLET FORMULATION

| | | mg/Tablet | | | | |
|---|---|---|---|---|---|---|
| Item | Ingredients | 5 mg | 25 mg | 100 mg | 250 mg | 500 mg | 750 mg |
| 1 | Compound A | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

Compound A represents a compound of the invention.

MANUFACTURING PROCEDURE

1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

EXAMPLE 10

CAPSULE FORMULATION

| | | mg/Tablet | | | | |
|---|---|---|---|---|---|---|
| Item | Ingredients | 5 mg | 25 mg | 100 mg | 250 mg | 500 mg |
| 1 | Compound A | 5 | 25 | 100 | 250 | 500 |
| 2 | Hydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

MANUFACTURING PROCEDURE

1. Mix Items 1, 2 and 3 in a suitable mixer for 15 minutes.
2. Add Items 4 & 5 and mix for 3 minutes.
3. Fill into a suitable capsule.

EXAMPLE 11

INJECTION SOLUTION/EMULSION PREPARATION

| Item | Ingredient | mg/mL |
|---|---|---|
| 1 | Compound A | 1 mg |
| 2 | PEG 400 | 10–50 mg |
| 3 | Lecithin | 20–50 mg |
| 4 | Soy Oil | 1–5 mg |
| 5 | Glycerol | 8–2 mg |
| 6 | Water | q.s. 1 mL |

MANUFACTURING PROCEDURE

1. Dissolve item 1 in item 2
2. Add items 3, 4 and 5 to item 6 and mix until until dispersed, then homogenize.

3. Add tffe solution from step 1 to the mixture from step 2 and homogenize until the dispersion is translucent.
4. Sterile filter through a 0.2 urn filter and fill into vials.

EXAMPLE 12

INJECTION SOLUTION/EMULSION PREPARATION

| Item | Ingredient | mg/mL |
|---|---|---|
| 1 | Compound A | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

MANUFACTURING PROCEDURE

1. Dissolve item 1 in item 2
2. Add items 3, 4 and 5 to item 6 and mix until until dispersed, then homogenize.
3. Add the solution from step 1 to the mixture from step 2 and homogenize until the dispersion is translucent.
4. Sterile filter through a 0.2 um filter and fill into vials.

We claim:

1. A pharmaceutical composition comprising an effective amount of a compound of the formula

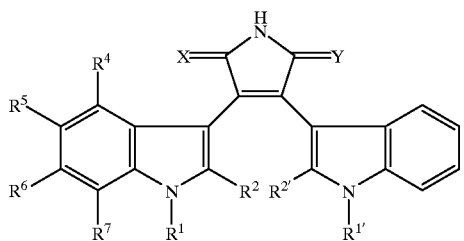

I wherein

R and $R^{1'}$ are independently alkyl, aryl, alkenyl or alkynyl;

$R^2$ and $R^{2'}$ are independently hydrogen or alkyl;

$R^4$, $R^5$, and $R^7$ each independently are

$CO_2R^9$, $CH_2OR^{10}$, CHO, $CH_2NR^{11}R^{12}$, $CON(R^{13})_2$, hydrogen, halogen, cyano, alkyl, hydroxy, alkoxy, aryloxy, haloalkyl, nitro, amino, acylamino, aralkyloxy, monoalkylamino, dialkylamino, alkylthio, alkylsulphinyl or alkylsulphonyl;

$R^6$ is $CO_2R^9$;

$R^8$ is alkyl, aralkyl or aryl;

$R^9$ is alkyl, aralkyl or aryl;

$R^{10}$ is hydrogen, alkyl, aralkyl or aryl;

$R^{11}$ and $R^{12}$ are independently hydrogen, alkyl, aryl, aralkyl or acyl;

$R^{13}$ is hydrogen, alkyl, aryl or aralkyl; and one of X and Y signifies O and the other signifies O, S, (H,OH) or (H,H); or pharmaceutically acceptable salts of acidic compounds of formula I with bases or basic compounds of formula I with acids.

2. A pharmaceutical composition of claim 1, wherein $R^1$ is alkyl.

3. A pharmaceutical composition of claim 2, wherein $R^1$ is methyl.

4. A pharmaceutical composition of claim 1, wherein $R^2$ is hydrogen.

5. A pharmaceutical composition of claim 1, wherein $R^{1'}$ is alkyl and $R^{2'}$ is hydrogen.

6. A pharmaceutical composition of claim 5, wherein $R^{1'}$ is methyl.

7. A pharmaceutical composition of claim 1, wherein $R^1$ alkyl, $R^2$ is hydrogen, $R^{1'}$ is alkyl, $R^{2'}$ is hydrogen, and $R^4$, $R^5$, $R^7$ are hydrogen.

8. A pharmaceutical composition of claim 7, wherein $R^9$ is alkyl.

9. A pharmaceutical composition of claim 8, wherein $R^9$ is methyl.

10. The pharmaceutical composition of claim 1, wherein the compound is Acetic acid 1-methyl-3-[4-(1-methyl-1H-indol- 3-yl)-2,5-dioxo-2,5-dihydro-1H-pyrro-3-yl]-1H-indol-6-yl methyl ester.

* * * * *